(12) United States Patent
Beck et al.

(10) Patent No.: US 8,197,438 B2
(45) Date of Patent: Jun. 12, 2012

(54) MEDICINAL FLUID DELIVERY SYSTEMS AND METHODS FOR PRIMING THE SAME

(75) Inventors: Timothy L. Beck, Pendleton, IN (US); Janette Allen, Indianapolis, IN (US); David Burke, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 42 days.

(21) Appl. No.: 12/646,501

(22) Filed: Dec. 23, 2009

(65) Prior Publication Data

US 2011/0152757 A1    Jun. 23, 2011

(51) Int. Cl.
*A61M 31/00* (2006.01)

(52) U.S. Cl. ......................................... 604/67
(58) Field of Classification Search .................. 604/65, 604/67, 131, 151
See application file for complete search history.

(56) References Cited

U.S. PATENT DOCUMENTS

| 4,410,322 | A |   | 10/1983 | Archibald |
| 5,103,817 | A | * | 4/1992  | Reisdorf et al. ......... 128/207.15 |
| 6,068,612 | A |   | 5/2000  | Bowman et al. |
| 6,142,008 | A |   | 11/2000 | Cole et al. |
| 6,159,186 | A |   | 12/2000 | Wickham et al. |
| 6,280,408 | B1 |  | 8/2001  | Sipin |
| 6,464,667 | B1 |  | 10/2002 | Kamen et al. |
| 6,475,178 | B1 |  | 11/2002 | Krajewski et al. |
| 6,554,791 | B1 |  | 4/2003  | Cartledge et al. |
| 6,558,346 | B1 |  | 5/2003  | Yoshioka et al. |
| 6,616,633 | B1 |  | 9/2003  | Butterfield et al. |
| 6,622,542 | B2 |  | 9/2003  | Derek et al. |
| 6,623,455 | B2 |  | 9/2003  | Small et al. |
| 7,727,181 | B2 | * | 6/2010  | Rush ................................. 604/67 |
| 7,993,108 | B2 | * | 8/2011  | Rush et al. .................. 417/199.2 |
| 2002/0016570 | A1 |  | 2/2002  | Cartledge |
| 2002/0019612 | A1 |  | 2/2002  | Watanabe et al. |
| 2002/0156383 | A1 | * | 10/2002 | Altman et al. ................ 600/508 |
| 2003/0004463 | A1 |  | 1/2003  | Reilly et al. |
| 2003/0007891 | A1 | * | 1/2003  | Wilson ............................ 422/56 |
| 2003/0040700 | A1 |  | 2/2003  | Hickle et al. |

(Continued)

FOREIGN PATENT DOCUMENTS

EP    1 762 263 A1    3/2007

(Continued)

OTHER PUBLICATIONS

PCT Partial International Search Report and Written Opinion dated May 11, 2011, PCT Application No. PCT/US2010/060949, filed Dec. 17, 2010, entitled Medicinal Fluid Delivery Systems and Methods for Priming the Same Applicant: Roche Diagnostics GmbH et al.

(Continued)

*Primary Examiner* — Nicholas D Lucchesi
*Assistant Examiner* — Aarti B Berdichevsky
(74) *Attorney, Agent, or Firm* — Dinsmore & Shohl LLP

(57) ABSTRACT

Medicinal fluid delivery systems and methods for priming the same are disclosed. The systems may be configured to measure an electro-transmissive quality of a medicinal fluid when: medicinal fluid is dispensed into a fluid delivery path, a proximal end of the fluid delivery path is in contact with a first electrode, and the distal end of the fluid delivery path is in contact with a second electrode. Methods for priming medicinal fluid delivery systems may include dispensing a medicinal fluid through a fluid delivery path, sensing an electro-transmissive quality of the medicinal fluid, and determining that the fluid delivery path is full based on the electro-transmissive quality.

19 Claims, 6 Drawing Sheets

U.S. PATENT DOCUMENTS

| | | | |
|---|---|---|---|
| 2003/0159741 A1 | 8/2003 | Sparks | |
| 2003/0167035 A1 | 9/2003 | Flaherty et al. | |
| 2004/0059295 A1 | 3/2004 | Cartledge et al. | |
| 2004/0204673 A1 | 10/2004 | Flaherty | |
| 2005/0235732 A1* | 10/2005 | Rush | 73/1.16 |
| 2005/0238503 A1* | 10/2005 | Rush et al. | 417/322 |
| 2010/0022988 A1* | 1/2010 | Wochner et al. | 604/506 |
| 2010/0185182 A1* | 7/2010 | Alme et al. | 604/891.1 |
| 2011/0137308 A1* | 6/2011 | Woloszko et al. | 606/41 |

FOREIGN PATENT DOCUMENTS

| | | |
|---|---|---|
| EP | 1 987 761 A1 | 11/2008 |
| WO | WO2006/027361 | 3/2006 |
| WO | 2006/113408 A2 | 10/2006 |
| WO | 2006/120253 A2 | 11/2006 |
| WO | WO2007/128144 | 11/2007 |

OTHER PUBLICATIONS

Partial European Search Report, Appl. No. EP 08 020 2099, Search Date Jul. 13, 2009, 5 pages.
ACCU-CHEK Spirit Pump User Guide, Sep. 2008, pp. 1-202.
International Search Report and Written Opinion dated Jul. 19, 2011 pertaining to International application No. PCT/US2010/060949.

* cited by examiner

MEDICINAL FLUID DELIVERY SYSTEMS AND METHODS FOR PRIMING THE SAME

TECHNICAL FIELD

Embodiments of the present disclosure generally relate to medicinal fluid delivery systems and, specifically, to priming the fluid delivery path of medicinal fluid delivery systems.

BACKGROUND

Persons suffering from diabetes may utilize an insulin pump to administer insulin medication. During the course of insulin pump therapy, the infusion set or the infusion site may be changed. Such changes often require that the infusion set be primed before further administration of insulin. Thus, the infusion set may need to be filled with insulin and be substantially free of air bubbles.

Accordingly, a need exists for alternative medicinal fluid delivery systems and alternative methods for priming the fluid delivery path of medicinal fluid delivery systems.

SUMMARY

It is against the above background that embodiments according to the present disclosure are provided which may be configured to measure an electro-transmissive quality of a medicinal fluid when: medicinal fluid is dispensed into a fluid delivery path, a proximal end of the fluid delivery path is in contact with a first electrode, and a distal end of the fluid delivery path is in contact with a second electrode. Methods for priming medicinal fluid delivery systems may include dispensing a medicinal fluid through a fluid delivery path, sensing an electro-transmissive quality of the medicinal fluid, and determining that the fluid delivery path is full based on the electro-transmissive quality.

In one embodiment, a medicinal fluid delivery system includes a medicinal fluid pump operably connected to a controller and fluidically connected to a tube including at least a portion of a fluid delivery path. The fluid delivery path includes a proximal end and a distal end. A first electrode may be in electrical communication with the controller, and a second electrode may be in electrical communication with the controller. The controller may be configured to measure an electro-transmissive quality of a medicinal fluid when: the pump dispenses the medicinal fluid into the fluid delivery path, the proximal end is in contact with the first electrode, and the distal end is in contact with the second electrode.

In another embodiment, a medicinal fluid delivery system includes a medicinal fluid pump operably connected to a controller, and a fluid delivery path at least partially within a tube. The tube may be in fluidic communication with the pump and the fluid delivery path includes a proximal end and a distal end. A first electrode may be disposed on the pump and in electrical communication with the controller, wherein the first electrode may be in contact with the proximal end. A second electrode may be disposed on the pump and in electrical communication with the controller, wherein when the second electrode may be in contact with the distal end. The pump may dispense a medicinal fluid into the fluid delivery path. The pump may be configured to reclaim any of the medicinal fluid that is dispensed beyond the distal end. The controller may be configured to: measure an electro-transmissive quality of the medicinal fluid, detect that the sterile fluid delivery path is filled with the medicinal fluid based on the electro-transmissive quality, detect a fluidic effervescence of the medicinal fluid based on the electro-transmissive quality, and reduce the fluidic effervescence of the medicinal fluid via a fluidic agitation or a fragmenting signal.

In still another embodiment, a method for priming a medicinal fluid delivery system may include: dispensing a medicinal fluid through a fluid delivery path at least partially within a tube, wherein the fluid delivery path includes a proximal end and a distal end; sensing an electro-transmissive quality of the medicinal fluid between a first electrode in contact with the proximal end and a second electrode in contact with the distal end; and determining that the fluid delivery path is full based on the electro-transmissive quality.

These and other embodiments of the present disclosure will become readily apparent to those skilled in the art from the following detailed description with reference to the attached figures, with no limitation to any particular embodiment(s) disclosed herein.

BRIEF DESCRIPTION OF THE DRAWINGS

The embodiments set forth in the drawings are illustrative and exemplary in nature and not intended to limit the embodiments defined by the claims. The following detailed description of the illustrative embodiments can be understood when read in conjunction with the following drawings, where, when possible, like structure is indicated with like reference numerals and in which:

DETAILED DESCRIPTION

Figure 1:
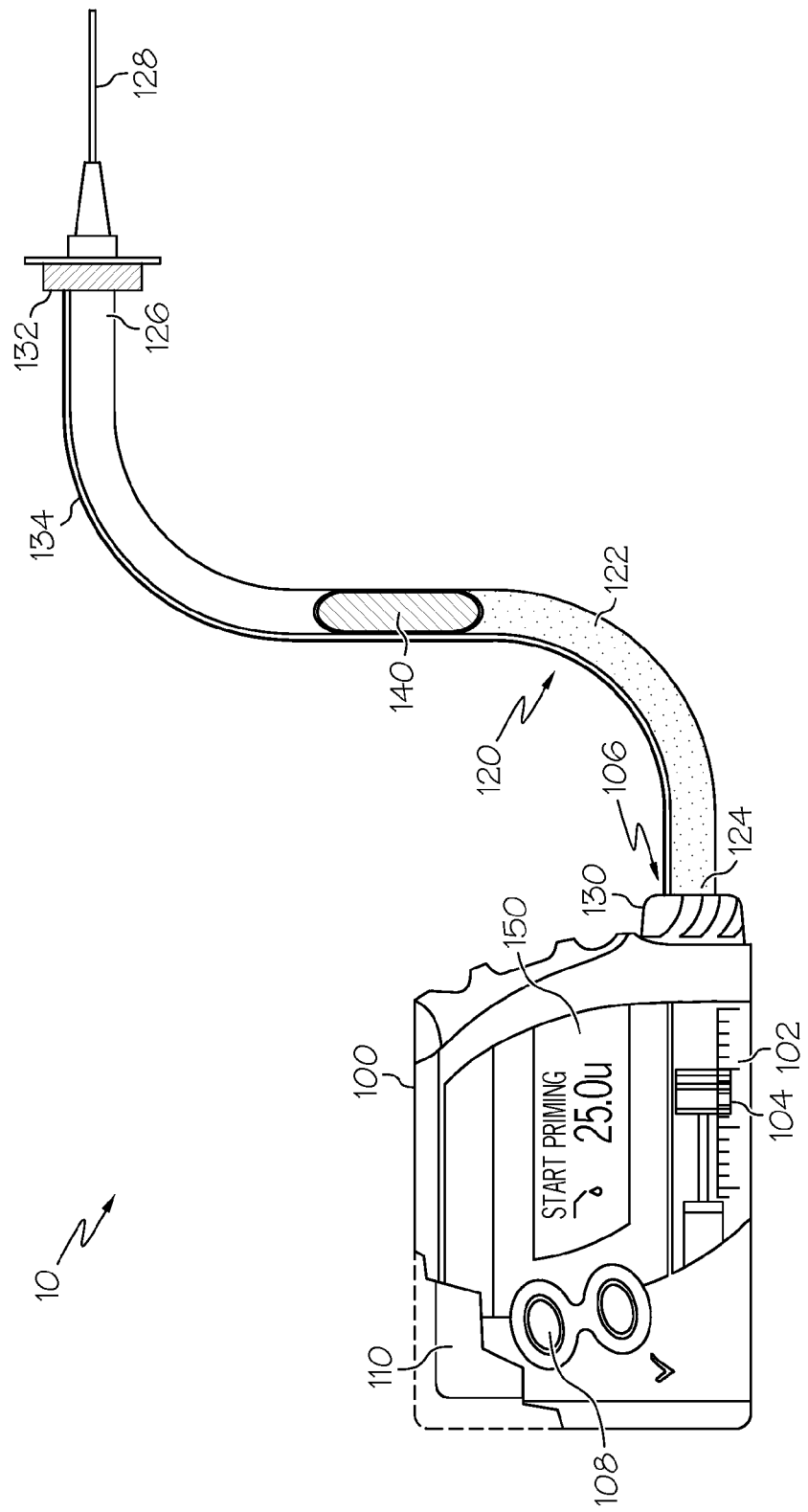
FIG. 1 depicts a medicinal fluid delivery system with multiple cut-away portions according to one or more embodiments shown and described herein.

The present specification will describe below various illustrative embodiments. Those skilled in the art will appreciate that the present specification may be implemented in a number of different applications and embodiments and is not specifically limited in its application to the particular embodiments depicted herein. In particular, the present specification will be discussed below in connection with systems and methods for priming a medicinal fluid delivery system comprising a pump, although those of ordinary skill will recognize that the present disclosure could be modified to be used with other types of medicinal delivery systems besides those comprising pumps such as for example, an intravenous drip.

As used herein with the various illustrated embodiments described below, the following terms include, but are not limited to, the following meanings.

The term "prime" means to fill a volume with a fluid in a manner such that the volume is substantially free of air, and the like.

The term "actuator" means a mechanism which displaces a fluid by physical or mechanical action such as for example, an impeller, a piston, a rotor, a compression member, and the like.

The term "contact" means to couple multiple electrical components for electrical communication via a conductive mechanism such as for example, terminal blocks, posts, solder joints, integrated circuit traces, wires, and the like.

The term "user interface" means a mechanism by which a user interacts with a system such as for example, a button, a switch, a touch screen, a roller ball, a voice command system, and the like.

The term "memory" means a storage device for retaining electronic data for later access such as for example, RAM, ROM, flash memory, hard drive, and the like.

The term "sterile" means substantially free of biological contaminants such that a medical device or fluid may be suitable for use.

The term "electro-transmissive quality" means a quantity inherent to a fluid that can be measured by optical or electrical mechanisms such as for example, interruption of a light path, circuit analysis, and the like.

The term "fluidic effervescence" means a quantity inherent to a contained volume of fluid that can be measured to provide information regarding undesired voids such as for example, air, gas, volumetric impurities, and the like.

The term "fragmenting signal" means a signal that can be induced to travel through an enclosed volume to remove undesired voids such as for example, an electrical signal, an ultrasonic signal, a wave, and the like.

The term "fluidic agitation" means a mechanical disturbance of a fluid that can remove undesired voids such as for example, an oscillation, a pressure change, a vibration, a translation, and the like.

The embodiments described herein generally relate to medicinal fluid delivery systems and methods for priming the same. As will be described in more detail herein, a medicinal fluid delivery system generally comprises a medicinal fluid pump, a fluid delivery path, a first electrode, a second electrode and a controller. The system may be arranged such that the pump is in fluidic communication with the fluid delivery path and the controller operates to dictate the operations of the pump. The first electrode and the second electrode may be in contact with portions of the fluid delivery path and in electrical communication with the controller. The operation and structure of embodiments of the present disclosure will be described in more detail below, with each of the above stated components described in turn.

As shown in FIG. 1, embodiments of the medicinal fluid delivery system 10 may comprise a medicinal fluid pump 100, or pump 100. The pump 100 may be a portable device, which may comprise a reservoir 102 for holding medicinal fluid 140, and an actuator 104, depicted as a plunger. The pump 100 may also comprise internal components (FIG. 5) such as, a memory 112, a controller 110, a user interface 108, and an alert indicator 150, an inlet 107 and an outlet 106, all of will be described in more detail herein. The pump 100 may be operable to dispense the medicinal fluid 140 either manually according to user input from the user interface 108 or automatically according to programmed instructions 114 stored in the memory 112. Whether by manual input or automatic instructions, the controller 110, as will be described in more detail below, may cause the actuator 104 to force the medicinal fluid 140 from the reservoir 102 through the outlet 106. For example, an insulin pump may automatically dispense insulin according to an automated schedule by causing a plunger to dispense insulin out of a syringe.

Figure 2:
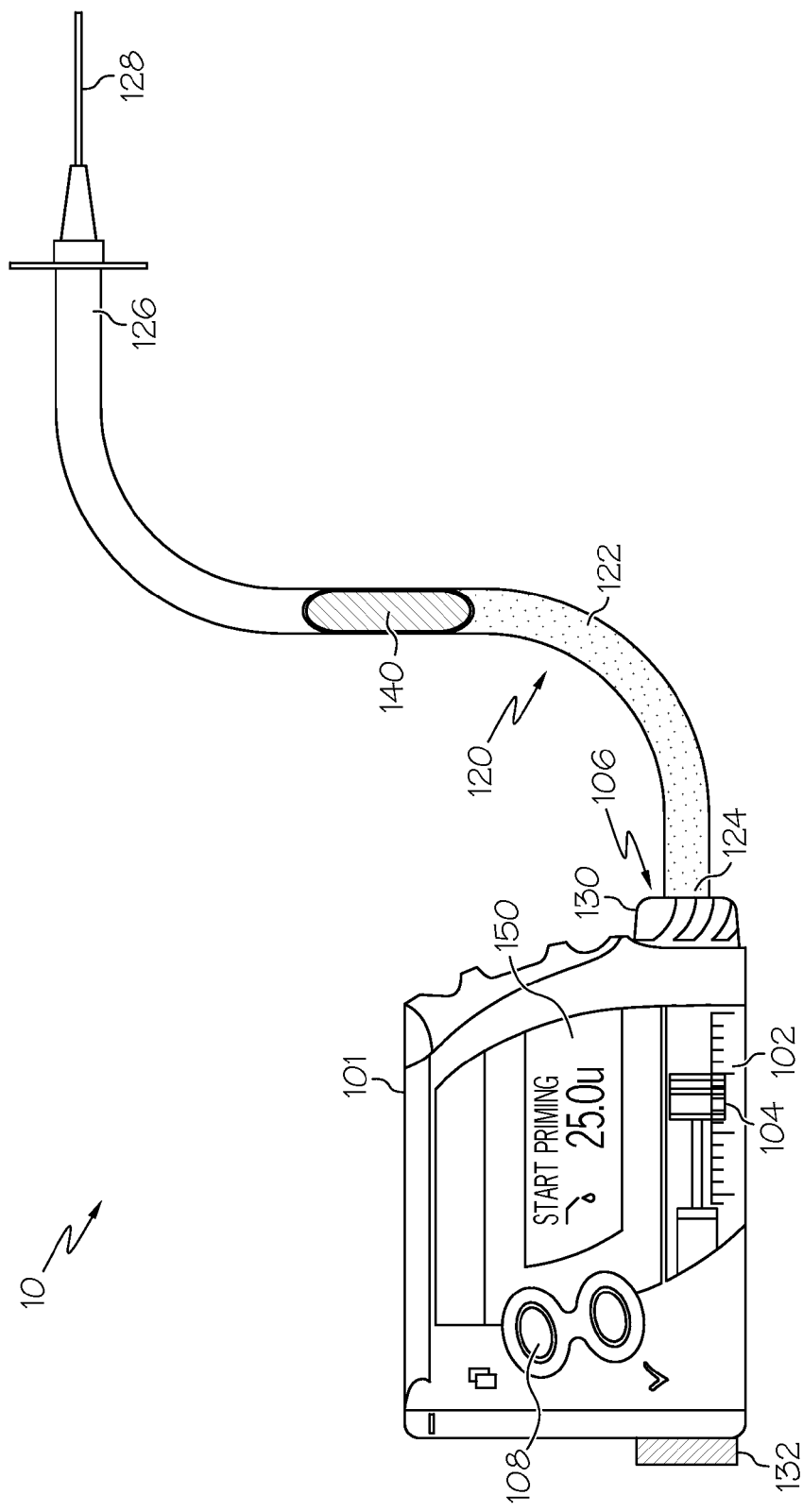
FIG. 2 depicts a medicinal fluid delivery system with a cut-away portion according to one or more embodiments shown and described herein.
Figure 3:
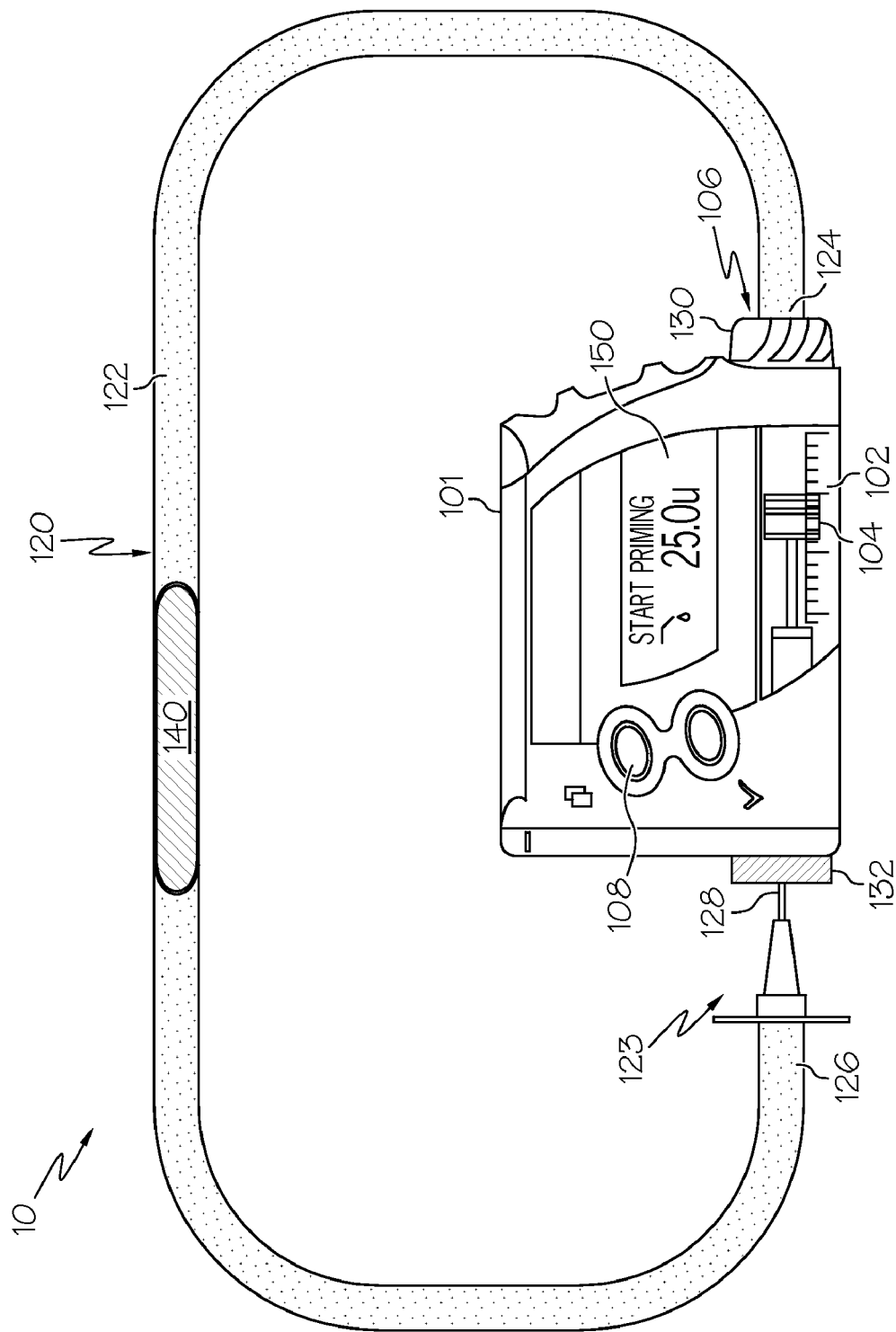
FIG. 3 depicts a medicinal fluid delivery system with a cut-away portion according to one or more embodiments shown and described herein.

Referring now to FIG. 1-3, embodiments may comprise a fluid delivery path 122. The fluid delivery path 122 may be a volumetric enclosure adapted for the transport of medicinal fluid 140 that spans from the outlet 106 of the medicinal fluid 140 to the delivery point 128. Further, the fluid delivery path 122 may comprise a proximal end 124 and a distal end 126. Such that, the proximal end 124 may be the portion of the fluid delivery path 122 nearest the outlet 106 and the distal end 126 may be the portion of the fluid delivery path 122 nearest the delivery point 128. For example, as shown in FIG. 1, the pump 100 may comprise the outlet 106 and the delivery point 128 may be configured for subcutaneous insertion, such as a cannula. It should be noted that, while the fluid delivery path 122 is depicted as being completely enclosed by a tube 120, it is contemplated that portions of the fluid delivery path 122 may be enclosed by other portions of the medicinal fluid delivery system 10, such as, but not limited to, the pump 100 (FIG. 1) or pump 101 (FIG. 2-3), or delivery point 128. Thus, less than the entire fluid delivery path 122 may be enclosed by the tube 120. It should be noted that the tube 120 may comprise an infusion set, for example, or any other enclosure suitable for the sterile transportation of medicinal fluid 140.

As described above, portions of the fluid delivery path 122 may be in contact with a first electrode 130 and a second electrode 132. Thus embodiments of the medicinal fluid delivery system 10 may comprise a first electrode 130 and a second electrode 132, as best seen in FIG. 1-3. The first electrode 130 and the second electrode 132, or electrodes 130/132, may comprise any material suitable for conducting electricity, such as copper, gold or any known or yet to be discovered conductive material. The electrodes may also comprise any shape such that they are configured to make electrical contact with the medicinal fluid 140 within the fluid delivery path 122. While the first electrode 130 and the second electrode 132 are depicted (FIG. 1) as cylindrical, the electrodes may comprise other shapes. For example, the electrodes may be alternatively configured to be surrounded by the medicinal fluid 140 within the fluid delivery path 122, as opposed to surrounding the medicinal fluid 140 (FIGS. 1-3), and thus, be pin-shaped or needle-shaped. It should be noted that, the above embodiments of the electrodes are merely illustrative in nature, and those of ordinary skill will recognize various alternative materials and shapes.

Since the electrodes may be in electrical communication with the controller, embodiments of the present disclosure may comprise a controller 110 (FIG. 1). While the controller 110 is depicted as a microprocessor, the controller 110 may be any type of computing device capable of executing programmed instructions 114, such as, but not limited to, a computer, a server, an integrated circuit, or silicon chip. Thus, with reference to FIG. 5, the controller 110 may be configured to communicate electronically (depicted as block arrows) to components such as: the memory 112, the actuator 104, the alert indicator 150, and the user interface 108. Such electronic communication may allow the controller 110 to receive instructions and dictate operations. And while the controller 110 is depicted in FIG. 1 and FIG. 5 as an integral component of the pump 100, it should be noted that the controller 110 may be a stand alone unit, such as a computer, with an operable connection with the pump 100 or pump 101 (FIG. 2-3) in embodiments of the present disclosure.

According to an embodiment of the present disclosure, FIG. 1 depicts a medicinal fluid delivery system 10. The medicinal fluid delivery system 10 may comprise a medicinal fluid pump 100 with an operable connection to a controller 110. The pump may comprise a reservoir 102, an actuator 104, an outlet 106 and an alert indicator 150. The pump 100 may be fluidically connected to a tube 120 such that at least a portion of a fluid delivery path 122 is within the tube 120. The fluid delivery path 122 may span from the outlet 106 through the delivery point 128, which may include any enclosure within the delivery point 128, and may comprise a proximal end 124 and a distal end 126. A first electrode 130 may be in contact with the proximal end 124, and a second electrode 132 may be in contact with the distal end 126, such that the first electrode 130 and the second electrode 132 are in electrical communication with the controller 110. The electrical communication between the electrodes 130 and 132 and the controller 110 may be via a conductive trace 134. The conductive trace 134 may comprise any material suitable for conducting electricity, as described hereinabove. While a conductive trace 134 is depicted as a wire running along the outside of the tube 120, it is contemplated that the conductive trace may be enclosed by the tube 120 or may be integral with the tube 120.

Referring now to FIG. 2-3, another embodiment of the medicinal fluid delivery system 10 is depicted. The medicinal fluid delivery system 10 may comprise a medicinal fluid pump 101 with an operable connection to a controller 110 (not shown in FIG. 2-3). The pump may comprise a reservoir 102, an actuator 104, an outlet 106, a first electrode 130, a second electrode 132 and an alert indicator 150. The pump 100 may be fluidically connected to a tube 120 such that at least a portion of a fluid delivery path 122 is within the tube 120. The fluid delivery path 122 may span from the outlet 106 to the delivery point 128, and may comprise a proximal end 124 and a distal end 126. The first electrode 130 may be in contact with the proximal end 124, and the second electrode may be configured to accept the delivery point 128. Further, the first electrode 130 and the second electrode 132 may be in electrical communication with the controller 110 (not shown in FIG. 2-3).

Figure 5:
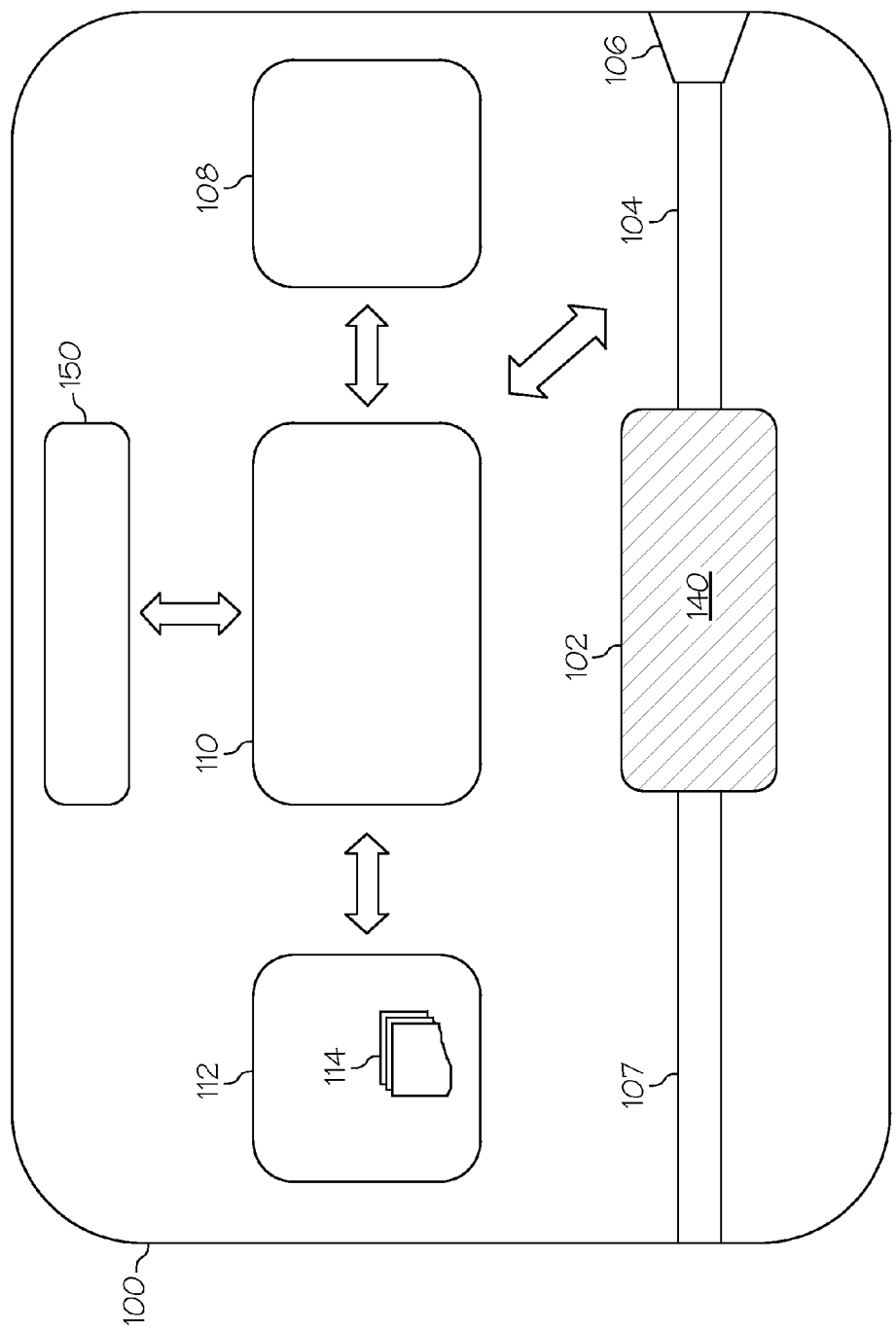
FIG. 5 depicts a block diagram of the internal components of a medicinal fluid pump according to one or more embodiments shown and described herein.

The controller 110, as shown in FIG. 5, may cause the pump 100 to dispense the medicinal fluid 140 from the reservoir 102 through the outlet 106 by, for example, causing the actuator 104 to translate, thus, forcing the medicinal fluid 140 from the reservoir 102. Such a dispensation may be initiated by a manual command, such as by pressing a user interface 108, depicted as a button in FIG. 1, or according to programmed instructions 114 (FIG. 5) stored on the memory 112 and electronically communicable to the controller 110, such as a basal dosing schedule. Referring now to FIG. 1, upon exiting the outlet 106, the medicinal fluid 140 may enter the fluid delivery path 122 at the proximal end 124. Thus a portion of the proximal end 124 can be filled with the medicinal fluid 140, and the first electrode 130 may be in contact with the proximal end 124 and the medicinal fluid 140. When such contact is made, some of the medicinal fluid 140 may be within the fluid delivery path 122 and between the first electrode 130 and the second electrode 132. As such, the controller 110 can measure an electro-transmissive quality of a medicinal fluid 140, as will be described in more detail below.

The electro-transmissive quality may be determined by, for example, but not limited to, creating an electrical potential difference between the first electrode 130 and the second electrode 132. Since, the first electrode 130 may be in contact with the proximal end 124, and the second electrode 132 may be in contact with the distal end 126, a current can be induced to travel through the medicinal fluid 140 between the two electrodes 130/132. For example, when the medicinal fluid 140 transitions from being in contact with only the proximal end 124 (FIG. 1-2) to being in contact with both electrodes 130/132 (FIG. 3), a change in magnitude of the current traveling between the electrodes 130/132 may occur. Such a transition may be analogous to the current flowing through an open compared to a closed electrical circuit, i.e. when medicinal fluid 140 appears at the second electrode 132 the circuit is closed. Thus when the controller 110 is in electrical communication with the electrodes, the controller 110 may be configured to detect that the fluid delivery path 122 is filled with the medicinal fluid 140 based on the electro-transmissive quality, for example by executing programmed instructions 114 stored on the memory 112 (FIG. 5). Similarly, with reference to FIG. 3, the controller 110 may be configured to detect that the fluid delivery path 122 is filled when the electro-transmissive quality corresponds to a change in impedance or admittance between the electrodes 130/132. Such a change, may be for example, a drop in impedance attributed to the medicinal fluid 140 after correcting for effects caused by the tube 120 that may contribute to the impedance, e.g. latent charges remaining within the tube 120. Furthermore, as described below, the controller may provide feedback regarding detections.

In embodiments of the present disclosure, the controller 110 (FIG. 1) can be configured to provide an indication that the fluid delivery path 122 is filled with medicinal fluid 140. For example, the controller 110 can provide an indication with the alert indicator 150, depicted as a display screen (FIG. 1-3), such that information is communicated with visible light, or the alert indicator 150 may be configured to provide the indication as an audible sound. In other embodiments, the alert indicator 150 may be configured to provide a tactile indication, such as, for example, a vibration. Additionally, the pump 100 (FIG. 1) or 101 (FIG. 2-3) may be configured to automatically stop dispensing the medicinal fluid 140 into the fluid delivery path 122 when the controller 110 (FIG. 1) detects that the fluid delivery path 122 is filled with the medicinal fluid 140, as described hereinabove.

Figure 4A:
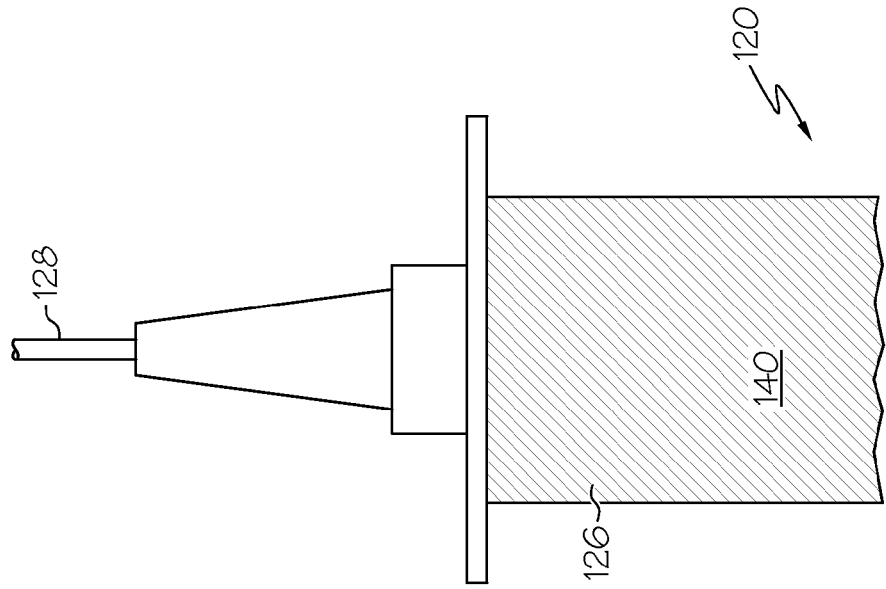
FIG. 4A depicts a partial cut-away view the distal end of a medicinal fluid delivery system according to one or more embodiments shown and described herein.

As disclosed in the preceding paragraphs, the electro-transmissive quality may be useful for the detection of a full fluid delivery path 122. Additionally, the electro-transmissive quality may also be useful for detecting the fluidic effervescence of the medicinal fluid 140. Therefore, embodiments of the medicinal fluid delivery system 10 may comprise a controller 110 configured to detect the fluidic effervescence of the medicinal fluid 140 based on the electro-transmissive quality. The controller may detect an electro-transmissive quality, such as, but not limited to an impedance. For example, as depicted in FIG. 4A, the medicinal fluid 140 may contain a number of air bubbles 142, and a high number of air bubbles 142 may equate to a high fluidic effervescence. Correspondingly, when the controller 110 (FIG. 1) is configured to measure impedance, a relatively high impedance value may equate to a high number of air bubbles 142, and, thus, a high fluidic effervescence. As such, the controller 110 may be configured to detect the fluidic effervescence of the medicinal fluid 140. Furthermore, as will be described in more detail below, the controller 110 may also be operative to execute actions according to the fluidic effervescence based on programmed instructions 114, for example causing the pump 100 to agitate the fluid or providing an indication with the alert indicator 150.

According to embodiments of the present disclosure, the controller 110 may be configured to reduce the fluidic effervescence of the medicinal fluid 140. As described herein, the fluidic effervescence is related to the number of air bubbles 142 (FIG. 4A) within the medicinal fluid 140, and may be reduced by reducing the number of air bubbles 142. The controller 110 (FIG. 1) may reduce the fluidic effervescence by transmitting a fragmenting signal, such as for example, a current, from the first electrode to the second electrode. Also, the controller 110 may cause the pump 100, or pump 101 (FIG. 2-3), to generate a fluidic agitation such that the number of air bubbles 142 (FIG. 4A) is reduced by, for example, oscillating the actuator 104 or dispensing more medicinal fluid 140. Alternatively, the pump 100 (FIG. 1), or pump 101 (FIG. 2-3), may be configured to reduce the fluidic effervescence via a fluidic agitation independent of the controller 110 (FIG. 1). In further embodiments, the pump 100 (FIG. 1), or pump 101 (FIG. 2-3), may be configured to reduce the fluidic effervescence via a manual agitation, such as, but not limited to, a physical manipulation of the medicinal fluid 140 by an external force. The above mechanisms for reducing the fluidic effervescence may occur manually or automatically, as will be described in more detail below.

Figure 4B:
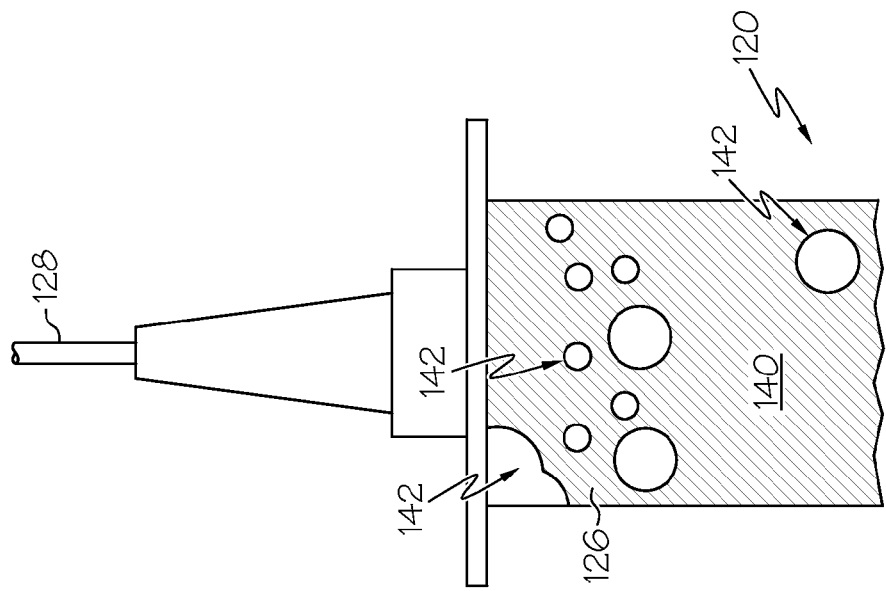
FIG. 4B depicts a partial cut-away view the distal end of a medicinal fluid delivery system according to one or more embodiments shown and described herein.

The controller 110 may be configured to automatically reduce the fluidic effervescence to an acceptable amount, such as, no air bubbles 142 as depicted in FIG. 4B. However, while FIG. 4B depicts no air bubbles, it should be noted that an acceptable level of fluidic effervescence may correlate to any amount of air bubbles 142 near zero, such as, no air bubbles 142 visible to the human eye, or a number of air bubbles 142 such that the administration of the medicinal fluid 140 is not compromised. Thus, the acceptable amount of fluidic effervescence may correspond to a threshold value stored in the memory 112 for a electro-transmissive quality and the controller 110 (FIG. 5) may be configured to automatically initiate one of the above described mechanisms for reducing the fluidic effervescence upon a failure to meet the threshold, or according to programmed instructions 114 stored on the memory 112. Similarly, the controller 110 may be configured to automatically provide an indication of a failure to meet the threshold with the alert indicator 150 (FIG. 1-3), detailed hereinabove.

Embodiments of the medicinal fluid delivery system 10 may be configured to reclaim medicinal fluid 140 that may be dispensed beyond the distal end 126 during the priming of the fluid delivery path 122. Therefore, as shown in FIG. 3, the medicinal fluid delivery system 10 may comprise a sterile fluid path 123 for the reclamation of medicinal fluid 140 by the pump 101. For example, when the tube 120 transitions from the unengaged position (FIG. 2) to an engaged position (FIG. 3) and creates a loop such that the delivery point 128 is within the pump 101, the proximal end 124 may be in contact with the first electrode 130 and the distal end 126 may be in contact with the second electrode 132. As such, a sterile fluid path 123 may be provided and the medicinal fluid 140 may be dispensed through the sterile fluid path 123 back into the reservoir 102 via the inlet 107 (FIG. 5), or any other storage location. Thus, referring back to FIG. 3, the pump 101 may be configured to reclaim any of the medicinal fluid 140 that may be dispensed beyond the distal end 126. It should be noted that, while the pump 101 is depicted as comprising both electrodes 130/132, embodiments of the present disclosure may provide for a sterile fluid path 123 without the pump 101 comprising any electrodes 130/132.

Figure 6:
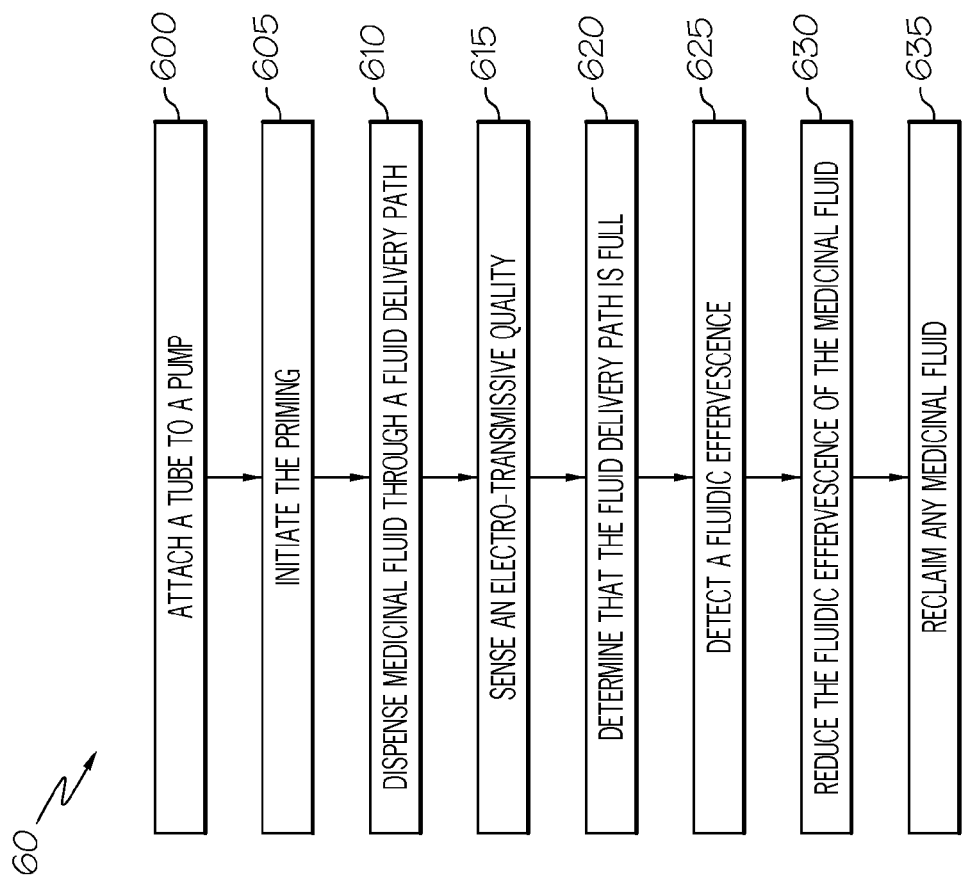
FIG. 6 depicts a method for priming a medicinal fluid delivery system according to one or more embodiments shown and described herein.

As described herein, embodiments of the medicinal fluid delivery system 10 may be operable such that the fluid delivery path 122 is primed according to programmed instructions 114 stored in the memory 112 and executed by the controller 110. FIG. 6 depicts a method 60 for priming embodiments of the medicinal fluid delivery system 10. At act 600, a user may attach a tube 120 to a pump 101. The tube 120 may be attached such that the proximal end 124 is in contact with the first electrode 130 and the distal end 126 is in contact with the second electrode 132. Additionally, in accordance with act 605, a user may initiate the priming. The priming may be initiated through interaction with the user interface 108 such as, but not limited to, pushing a "prime" button. As such, the initiation may cause the controller 110 to follow a priming procedure according to programmed instructions 114 stored on in the memory 112.

At act 610, the pump 101 may dispense medicinal fluid 140 through a fluid delivery path 122. After dispensing, the fluid delivery path 122, which may be at least partially within the tube 120, may contain medicinal fluid 140 between the proximal end 124 and the distal end 126. At act 615, the controller 110 may sense an electro-transmissive quality, as described in detail above. Based on the electro-transmissive quality, the controller 110 may determine that the fluid delivery path 122 is full, as in act 620. Thus, the fluid delivery path 122 may be filled with medicinal fluid 140 and the controller 110 may store the electro-transmissive quality in memory 112 or provide an indication relating to the fullness of the fluid delivery path 122, as detailed hereinabove.

In addition to making such a determination, the controller 110 may detect a fluidic effervescence in accordance with act 625. For example, the controller 110 may sense the impedance of the medicinal fluid 140 and make a comparison with information stored on the memory 112 to calculate the fluidic effervescence. Upon calculating the fluidic effervescence, the controller 110 may complete an operation according to programmed instructions 114 stored in memory 112, such as for example, storing the fluidic effervescence in memory 112, or providing an indication, as described above.

Additionally, in accordance with act 630, the controller 110 may reduce the fluidic effervescence of the medicinal fluid 140. The reduction may be accomplished by transmitting a fragmenting signal from the first electrode 130 to the second electrode 132, or agitating the medicinal fluid 140, as described herein. Upon such a reduction the fluidic effervescence of the medicinal fluid 140 may be reduced such that that the tube 120 is suitable for subcutaneous insertion. Further, the pump 101 may reclaim any medicinal fluid 140, act 635, such that medicinal fluid 140 that may be dispensed out of the fluid delivery path 122 during priming can be reused. For example, the distal end 126 may be inserted into the inlet 107 during priming, and the medicinal fluid 140 dispensed past the distal end 126 may flow through the inlet 107 for storage in the reservoir 102.

It should now be understood that various embodiments of the medicinal fluid delivery system 10 may be configured to assist in the priming of a fluid delivery path 122, which may comprise a cannula, with insulin. For example, an infusion set may be attached to an insulin pump. The insulin pump may begin priming the infusion set when a "prime" button is pushed. The insulin pump, as described hereinabove, may be configured to detect that the infusion set is filled with insulin and free of air bubbles, such that insulin extends out of the end of the cannula. The insulin pump may be further configured to provide a sterile path to reclaim insulin that is dispensed beyond the cannula during priming for reuse.

Thus, embodiments of medicinal fluid delivery systems and methods for priming the same are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A medicinal fluid delivery system comprising:
   a controller configured to detect when a fluid delivery path is volumetrically full with a medicinal fluid;
   a medicinal fluid pump operably connected to the controller and fluidically connected to a tube comprising at least a portion of the fluid delivery path, wherein the fluid delivery path comprises a proximal end and a distal end;
   a first electrode in electrical communication with the controller; and
   a second electrode in electrical communication with the controller wherein, the controller is configured to measure an electro-transmissive quality of the medicinal fluid when:
      the pump dispenses the medicinal fluid into the fluid delivery path;
      the proximal end is in contact with the first electrode; and
      the distal end is in contact with the second electrode;
   wherein the controller is further configured to provide an indication that the entire fluid delivery path from the proximal end to the distal end is volumetrically full when the controller detects that the entire fluid delivery path is volumetrically full with the medicinal fluid.

2. The system of claim 1 wherein the indication is tactile, an audible sound or a visible light.

3. The system of claim 1 wherein the pump is configured to automatically stop dispensing the medicinal fluid into the fluid delivery path when the controller detects that the fluid delivery path is volumetrically full with the medicinal fluid.

4. The system of claim 1 wherein the controller is configured to detect that the fluid delivery path is volumetrically full with the medicinal fluid based on the electro-transmissive quality.

5. The system of claim 4 wherein the electro-transmissive quality is a current, an impedance or an admittance.

6. The system of claim 1 wherein the controller is configured to detect a fluidic effervescence of the medicinal fluid based on the electro-transmissive quality.

7. The system of claim 6 wherein the controller is configured to reduce the fluidic effervescence of the medicinal fluid via a fluidic agitation or by transmitting a fragmenting signal from the first electrode to the second electrode.

8. The system of claim 6 wherein the controller is configured to provide an alert based on the fluidic effervescence of the medicinal fluid.

9. The system of claim 6 wherein the controller is configured to detect that the fluid delivery path is volumetrically full with the medicinal fluid based on the electro-transmissive quality.

10. The system of claim 1 wherein the pump is configured to provide a sterile fluid path when the proximal end is in contact with the first electrode and the distal end is in contact with the second electrode.

11. The system of claim 10 wherein the pump is configured to reclaim any of the medicinal fluid that is dispensed beyond the distal end.

12. The system of claim 11 wherein the pump comprises the first electrode and the second electrode.

13. A medicinal fluid delivery system comprising:
    a medicinal fluid pump operably connected to a controller;
    a fluid delivery path at least partially within a tube wherein, the tube is in fluidic communication with the pump and the fluid delivery path comprises a proximal end and a distal end;
    a first electrode disposed on the pump and in electrical communication with the controller, wherein the first electrode is in contact with the proximal end; and
    a second electrode disposed on the pump and in electrical communication with the controller, wherein when the second electrode is in contact with the distal end and the pump dispenses a medicinal fluid into the fluid delivery path, the controller is configured to:
       measure an electro-transmissive quality of the medicinal fluid;
       detect that the fluid delivery path is filled with the medicinal fluid based on the electro-transmissive quality;
       detect a fluidic effervescence of the medicinal fluid based on the electro-transmissive quality; and
       reduce the fluidic effervescence of the medicinal fluid via a manual agitation, a fluidic agitation or a fragmenting signal.

14. The system of claim 13 wherein the pump is configured to reclaim any of the medicinal fluid that is dispensed beyond the distal end.

15. A method for priming a medicinal fluid delivery system comprising:
    dispensing a medicinal fluid through a fluid delivery path at least partially within a tube, wherein the fluid delivery path comprises a proximal end and a distal end;
    sensing an electro-transmissive quality of the medicinal fluid between a first electrode in contact with the proximal end and a second electrode in contact with the distal end; and
    determining that the fluid delivery path is full based on the electro-transmissive quality.

16. The method of claim 15 further comprising reclaiming any of the medicinal fluid that is dispensed beyond the distal end.

17. The method of claim 15 further comprising:
    detecting a fluidic effervescence of the medicinal fluid based on the electro-transmissive quality.

18. The method of claim 17 further comprising:
    transmitting a fragmenting signal from the first electrode to the second electrode; and
    reducing the fluidic effervescence of the medicinal fluid.

19. The method of claim 17 further comprising:
    agitating the medicinal fluid; and
    reducing the fluidic effervescence of the medicinal fluid.

* * * * *

UNITED STATES PATENT AND TRADEMARK OFFICE
CERTIFICATE OF CORRECTION

| | | |
|---|---|---|
| PATENT NO. | : 8,197,438 B2 | Page 1 of 1 |
| APPLICATION NO. | : 12/646501 | |
| DATED | : June 12, 2012 | |
| INVENTOR(S) | : Timothy L. Beck et al. | |

It is certified that error appears in the above-identified patent and that said Letters Patent is hereby corrected as shown below:

Col. 2, Line 38, "view the" should read --view of the--;

Col. 2, Line 41, "view the distal" should read --view of the distal--;

Col. 3, Line 59, "all of will be" should read --all of which will be--;

Col. 7, Line 28, "a electro-transmissive" should read --an electro-transmissive--;

Col. 10, Line 20, Claim 13, "delivery path is filled" should read --delivery path is volumetrically full--;

Col. 10, Line 24, Claim 13, "quality; and" should read --quality;--;

Col. 10, Line 27, Claim 13, "signal." should read --signal; and
provide an indication that the entire fluid delivery path from the proximal end to the distal end is volumetrically full when the controller detects that the entire fluid delivery path is volumetrically full with the medicinal fluid.--;

Col. 10, Line 40, Claim 15, "path is full" should read --path is volumetrically full--; and Col. 10, Line 41, Claim 15, "quality." should read
--quality of the medicinal fluid when a controller that is configured to provide an indication that the entire fluid delivery path from the proximal end to the distal end is volumetrically full detects that the entire fluid delivery path is volumetrically full with the medicinal fluid.--.

Signed and Sealed this
Twenty-fifth Day of September, 2012

David J. Kappos
*Director of the United States Patent and Trademark Office*